US012691192B2

(12) United States Patent
Anand et al.

(10) Patent No.: US 12,691,192 B2
(45) Date of Patent: Jul. 28, 2026

(54) UV-C STERILIZATION APPARATUS AND METHOD

(71) Applicant: ANAND NVH PRODUCTS INC., Novi, MI (US)

(72) Inventors: Armaan A. Anand, New Delhi (IN); Sirhaan Seth, Gurugram (IN); Reyhaan Seth, Gurugram (IN)

(73) Assignee: ANAND NVH PRODUCTS INC., Novi, MI (US)

( * ) Notice: Subject to any disclaimer, the term of this patent is extended or adjusted under 35 U.S.C. 154(b) by 0 days.

(21) Appl. No.: 18/200,749

(22) Filed: May 23, 2023

(65) Prior Publication Data

US 2023/0293747 A1     Sep. 21, 2023

Related U.S. Application Data

(62) Division of application No. 17/098,714, filed on Nov. 16, 2020, now Pat. No. 11,690,925.

(51) Int. Cl.
A61L 2/10          (2006.01)

(52) U.S. Cl.
CPC ............. A61L 2/10 (2013.01); *A61L 2202/11* (2013.01); *A61L 2202/123* (2013.01); *A61L 2202/14* (2013.01); *A61L 2202/25* (2013.01)

(58) Field of Classification Search
CPC .... A61L 2/10; A61L 2202/14; A61L 2202/25; A61L 2202/11; A61L 2202/123
See application file for complete search history.

(56) References Cited

U.S. PATENT DOCUMENTS 10,145,055 B1     12/2018   Harlan et al.
2021/0347705 A1*  11/2021   Goodman ............... C05F 17/30

FOREIGN PATENT DOCUMENTS

CN     105883083          8/2016
CN     206063447  U  *   4/2017
                  (Continued)

OTHER PUBLICATIONS

English Translation for CN 206063447 U (Year: 2017).*

*Primary Examiner* — Sean E Conley
(74) *Attorney, Agent, or Firm* — Dickinson Wright PLLC

(57)          ABSTRACT

A UV-C sterilization apparatus for a confined space having a closure which can be selectively positioned between a closed position, wherein the confined space is fully enclosed, and an opened position, wherein the confined space is accessible from an exterior thereof. The apparatus comprises means for connecting the apparatus to a power source to provide operating power to the apparatus and a housing dimensioned to fit within the confined space. The housing supports at least one sensor operative to detect when the closure is in the closed position and/or when the closure is not in the closed position; at least one source operative to emit UV-C light for irradiating the confined space; and a controller. The controller is connected to the at least one sensor and the at least one UV-C light source, and is operative to: determine when the closure is and is not in the closed position; activate the at least one UV-C light source to irradiate the confined space for a first fixed period of time when it is determined that the closure has gone to the closed position from not being in the closed position; periodically activate the UV-C light source to irradiate the confined space for at least a second fixed period of time, the periodic activation occurring following the first fixed period of time for so long as the closure remains in the closed position; and prevent the at least one UV-C light source from irradiating the confined space when it is determined that the closure is not in the closed position.

16 Claims, 10 Drawing Sheets

(56)        References Cited

FOREIGN PATENT DOCUMENTS

| | | |
|---|---|---|
| CN | 209204143 U | 8/2019 |
| CN | 111214679 | 6/2020 |
| CN | 111214679 A | 6/2020 |
| DE | 202012102250 | 11/2012 |
| DE | 202012102250 U1 | 11/2012 |
| GB | 2595317 | 11/2021 |
| WO | WO2021262751 | 12/2021 |

* cited by examiner

UV-C STERILIZATION APPARATUS AND METHOD

CROSS-REFERENCE TO RELATED APPLICATIONS

The present application is a divisional application of U.S. patent application Ser. No. 17/098,714, filed 16 Nov. 2002 and issued 4 Jul. 2023 as U.S. Pat. No. 11,690,925, the disclosure of which is incorporated herein by reference in its entirety.

FIELD OF THE INVENTION

The present invention pertains to the field of UV-C sterilization and, more particularly, to a UV-C sterilization apparatus and method which functions to provide programmed irradiation of a confined space in response to the opening/closing of a closure for the confined space.

BACKGROUND

Ultraviolet radiation in the 200-300 nanometer (nm) range, also referred to as UV-C light, is effective at killing microorganisms such as airborne and surface bacteria, viruses, yeasts, and molds. A germicidal effectiveness curve (based upon the effect of various wavelengths of radiation on a common bacterium) indicates a peak of photic absorption by the bacterial DNA at 254 nm. There are commercially available light sources that generate UV light in the wavelength range of about 200 nm to about 300 nm, which encompasses the effectiveness peak.

With the recent occurrence of the global COVID-19 pandemic, interest in UV-C sterilization has been renewed.

While UV light is helpful in sterilizing surfaces, overexposure can be harmful to humans. Studies have shown ill effects of overexposure to UV rays found in solar energy. Similarly, overexposure to lamp-emitted germicidal UV radiation can cause erythema of the skin similar to sunburn, and direct exposure to the eyes can cause painful inflammation of the conjunctiva, cornea and iris, or even lasting damage.

Precautionary measures are therefore reduce the risk of accidental or uninformed exposure to UV radiation.

To date, many UV-C sterilization apparatus have been incorporated into building ventilation systems to provide sterilized air throughout the building. Such fixed installation are complex in construction and of limited value in providing sterilization of objects within individual rooms in the building.

Still other UV-C sterilization apparatus in the prior art are portable and take the form of a small enclosed container dimensioned to receive a single object to be sterilized, such as a mobile phone. These apparatus are obviously of very limited utility.

There thus remains room to improve upon the utility of UV-C sterilization apparatus.

SUMMARY OF THE DISCLOSURE

Disclosed herein is a UV-C sterilization apparatus for a confined space The confined space has a closure which can be selectively positioned between a closed position, wherein the confined space is fully enclosed, and an opened position, wherein the confined space is accessible from an exterior thereof. The UV-C sterilization apparatus comprises a housing dimensioned to fit within the confined space, the housing supporting at least one sensor operative to detect when the closure is in the closed position and/or the opened position; at least one source operative to emit UV-C light for irradiating the confined space; a controller; and means for connecting the apparatus to a power source to provide operating power to the apparatus. The controller is operative to: determine from the at least one sensor when the closure is in the closed position and the opened position; activate the at least one UV-C light source to irradiate the confined space for a first fixed period of time when it is determined that the closure has gone from the opened position to the closed position; periodically activate the at least one UV-C light source to irradiate the confined space for at least a second fixed period of time, the periodic activation occurring following the first fixed period of time for so long as the closure remains in the closed position; and prevent the at least one UV-C light source from irradiating the confined space when it is determined that the closure has gone from the closed position to the opened position.

Per one embodiment, the means for connecting the apparatus to a power source are operative to connect the apparatus to one or more batteries disposed in the housing.

In another embodiment, the means for connecting the apparatus to a power source are operative to connect the apparatus to one or more rechargeable batteries disposed in the housing.

Per another embodiment, the means for connecting the apparatus to a power source are operative to connect the apparatus to a power source external to the apparatus.

In one aspect, the confined space is one of a glovebox or a center console in a passenger automobile; the external power source may be the automobile's battery, to which the apparatus is connected by means of a conventional wiring harness. The closure may be manually and/or automatically operable to move between the opened and closed positions.

In one embodiment, the housing supports at least three UV-C light sources arranged to emit UV-C light in different directions relative to each other. In one aspect, the housing is characterized in that the at least three UV-C light sources are each positioned in a surface of the housing which is oriented at a different angle relative to the others of the UV-C light sources.

According to one feature, the at least one sensor is a photosensor. The photosensor may, in one form thereof, be a photoresistor. Also per this feature, the controller is programmed to determine the closure to be in the closed position when the electrical resistance through the photoresistor increases to at least a first predetermined value, and to determine the closure to be in the open position when the electrical resistance through the photoresistor decreases to a value greater than a predefined percentage of deviation from the first predetermined value. In an exemplary embodiment, the percentage of deviation is approximately 5%.

Per another feature, the apparatus has a calibration mode for establishing the first predetermined electrical resistance value. According to this calibration mode, the controller is operative to measure the electrical resistance through the photoresistor during a finite period of time when the closure is in the closed position, and to establish the first predetermined electrical resistance value as an electrical resistance measurement taken during said finite period of time. The finite period of time may, for instance, be approximately 10 seconds.

According to one embodiment, the finite period of time is preceded by a predefined period of time—e.g., 10 seconds—allowing for the closure to be moved to the closed position.

Per one embodiment, the controller is programmed with an electrical resistance "ceiling" value, and is further programmed to (a) compare the electrical resistance "ceiling" value with the measured electrical resistance at the start of the finite period of time, and (b) terminate the calibration mode without establishing the first predetermined electrical resistance value if the measured electrical resistance at the start of the finite period of time is equal to or less than the "ceiling" value.

In one aspect, the confined space has cubic dimensions of approximately 2 feet or less, and the first fixed period of time is approximately 3 minutes. The second period of time may, in another aspect, also be approximately 3 minutes, and the period of activation of the at least one UV-C light source is approximately every 60 minutes.

The present disclosure also comprehends a method for UV-C sterilization of a confined space having a closure which can be selectively positioned between a closed position, wherein the confined space is fully enclosed, and an opened position, wherein the confined space is accessible from an exterior thereof. The method comprises the following steps:

Providing a UV-C sterilization apparatus within the confined space, the apparatus including a housing dimensioned to fit within the confined space, the housing supporting at least one sensor operative to detect when the closure is the closed position and/or the opened position, at least one source operative to emit UV-C light for irradiating the confined space, and a controller. A power source provides operating power to the apparatus. The controller is operative to determine from the at least one sensor when the closure is in the closed position and the opened position, to selectively activate the at least one UV-C light source, and to selectively prevent the at least one UV-C light source from irradiating the confined space.

Activating the at least one UV-C light source to irradiate the confined space for a first fixed period of time when the controller determines that the closure has gone from the opened position to the closed position; Periodically activating the at least one UV-C light source to irradiate the confined space for at least a second fixed period of time, the periodic activation occurring following the first fixed period of time for so long as the closure remains in the closed position.

Preventing the at least one UV-C light source from irradiating the confined space when the controller determines that the closure has gone from the closed position to the opened position.

In one embodiment, the at least one sensor is a photoresistor and the controller is programmed to determine the closure to be in the closed position when the electrical resistance through the photoresistor increases to at least a first predetermined value, and to determine the closure to be in the open position when the electrical resistance through the photoresistor decreases to a value greater than a predefined percentage of deviation from the first predetermined value. Per one aspect, the predefined percentage of deviation is approximately 5%.

According to one feature, the method comprises a calibration step for establishing the first predetermined electrical resistance value. According to this calibration step, the controller measures the electrical resistance through the photoresistor during a finite period of time when the closure is in the closed position, and establishes the first predetermined electrical resistance value as an electrical resistance measurement taken during said finite period of time. The finite period of time may be, for instance, approximately 10 seconds.

stepper one embodiment, the finite period of time is preceded by a predefined period of time—e.g., 10 second—allowing for the closure to be moved to the closed position.

In one embodiment, the controller is programmed with an electrical resistance "ceiling" value. During the calibration step, the controller (a) compares the electrical resistance "ceiling" value with the measured electrical resistance at the start of the finite period of time, and (b) terminates the calibration mode without establishing the first predetermined electrical resistance value if the measured electrical resistance at the start of the finite period of time is equal to or less than the "ceiling" value.

According to one embodiment, the confined space is approximately 2 cubic feet or less, the first fixed period of time is approximately three minutes, and the second fixed period of time is approximately three minutes. The period activation of the at least one UV-C light source is approximately every 60 minutes.

WRITTEN DESCRIPTION

Figure 1:
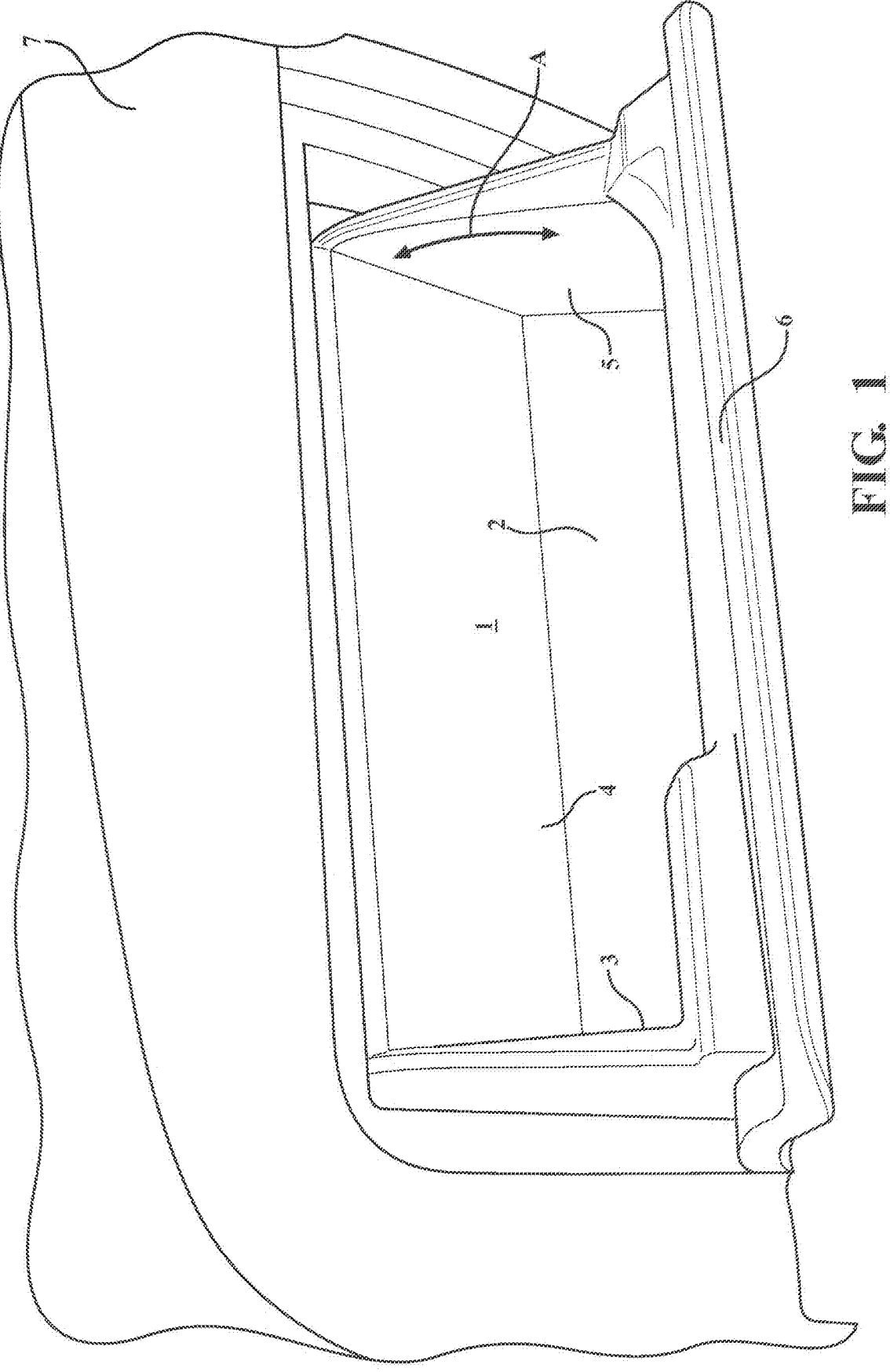
FIG. 1 depicts a conventional automobile glovebox as an example of a confined space of the type suited to employment of the sterilization apparatus of the present invention.
Figure 2:
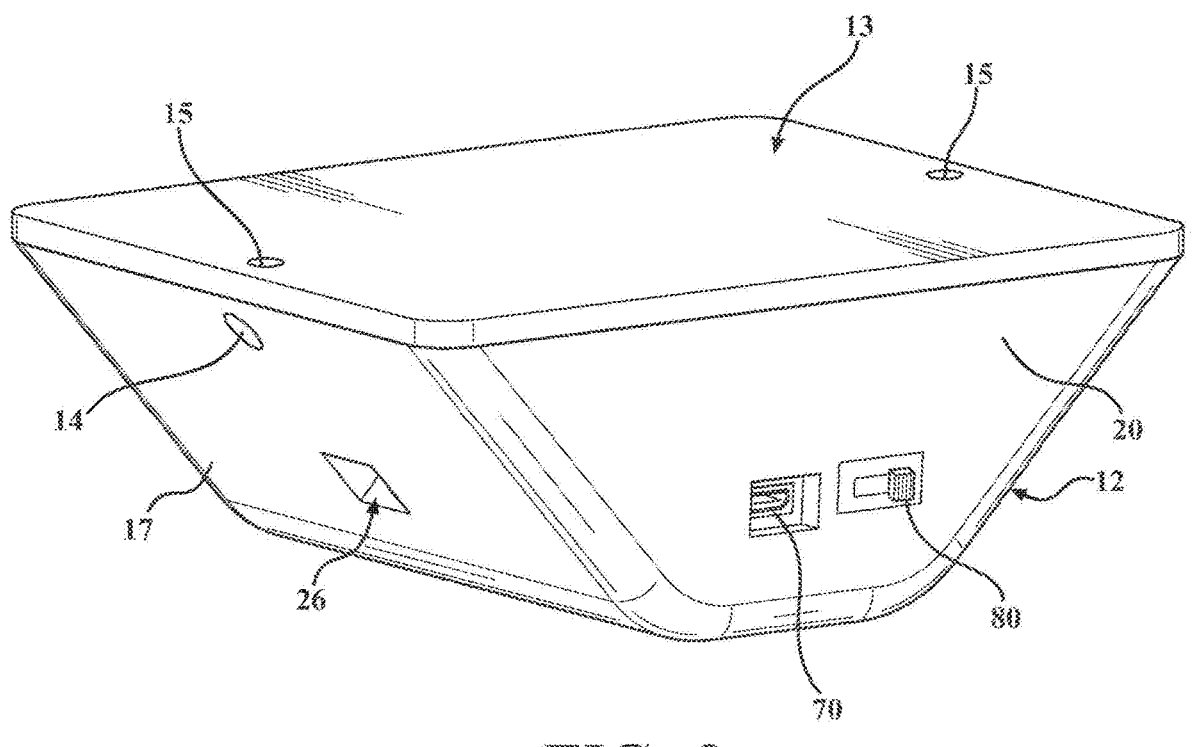
FIG. 2 is a quartering perspective view of the sterilization apparatus of the present invention.
Figures 3, 4:
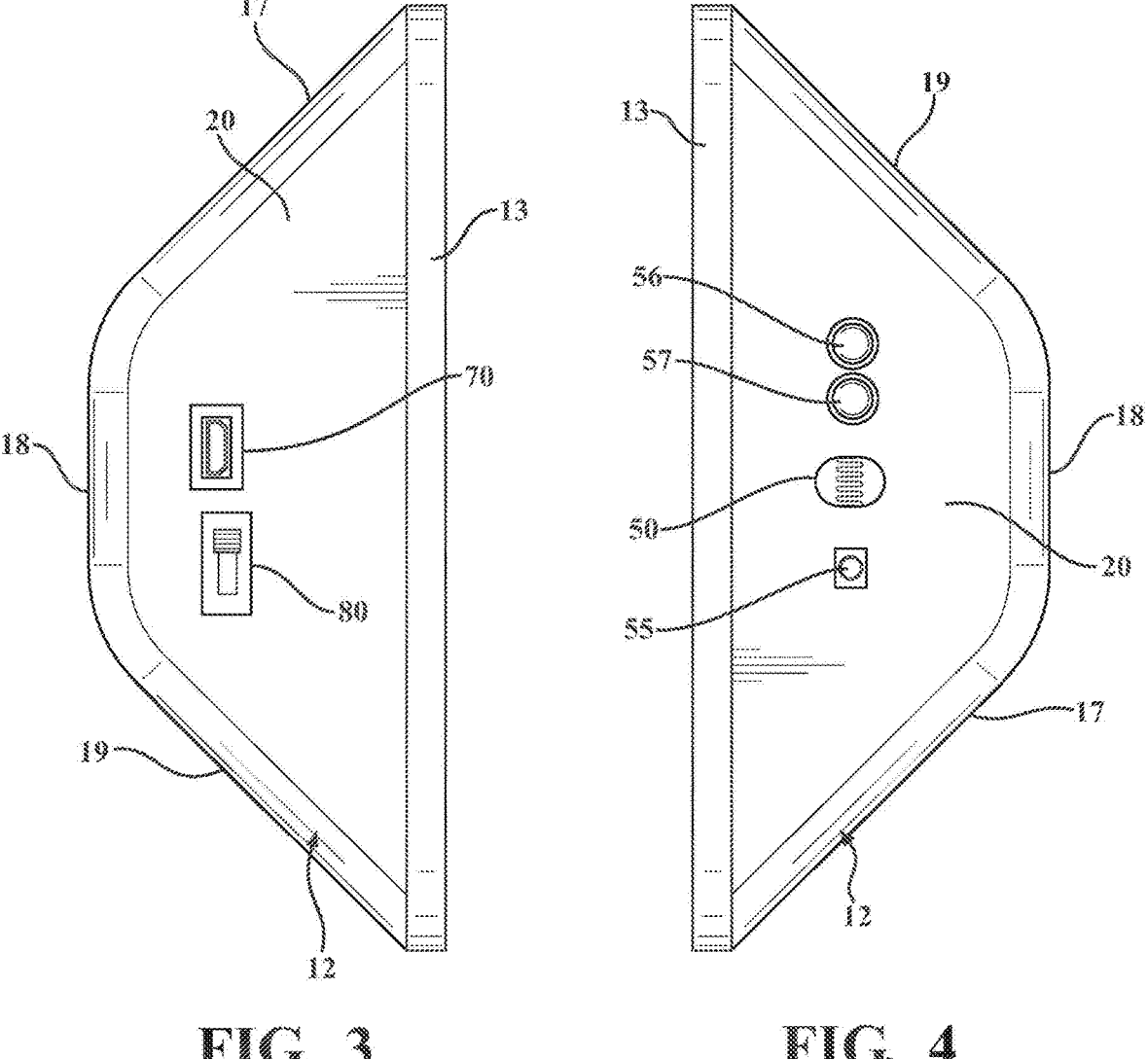
FIG. 3 is a lateral view of the sterilization apparatus of the FIG. 2.
FIG. 4 is a lateral view of the sterilization apparatus of the FIG. 2, showing the side of the apparatus opposite that shown in FIG. 3.
Figure 5:
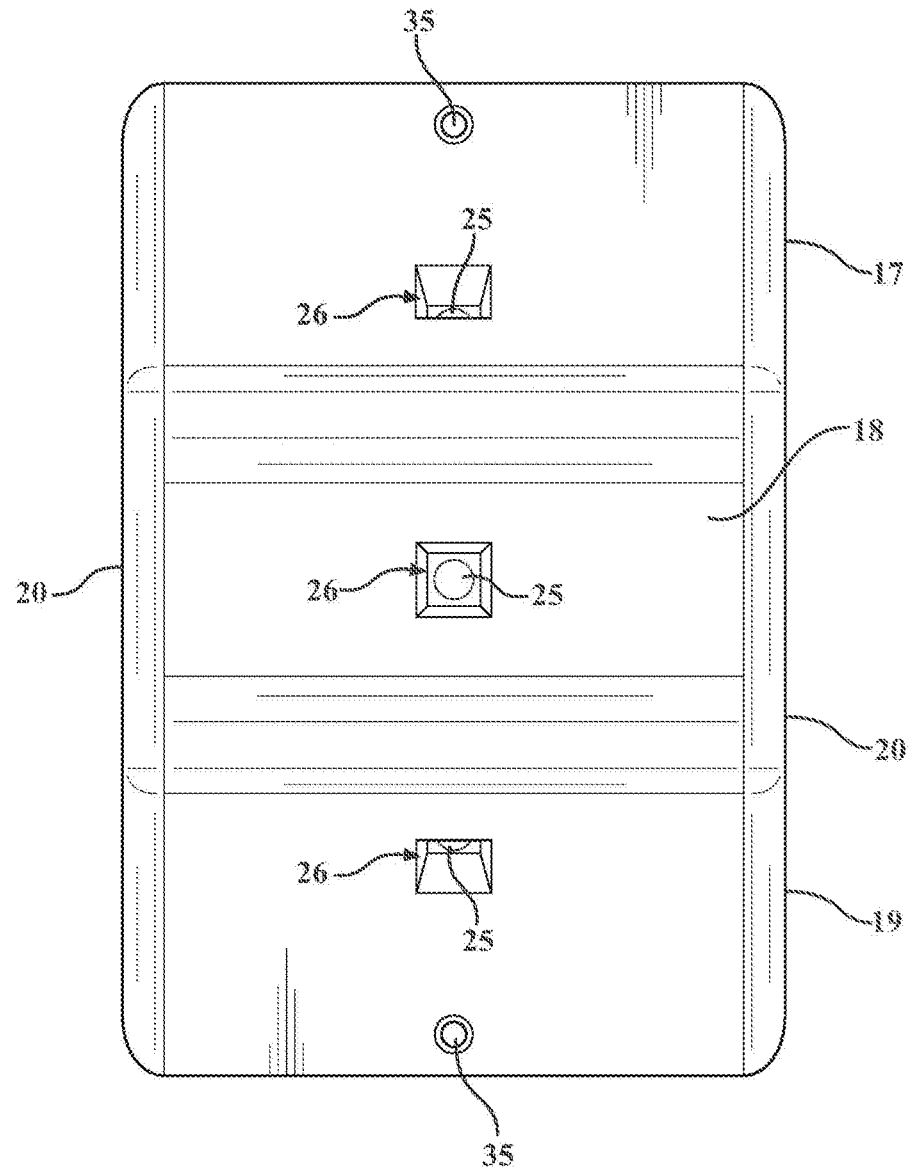
FIG. 5 is a bottom view of the sterilization apparatus of the FIG. 2, showing the surface thereof through which UV-C light emanates.
Figure 6:
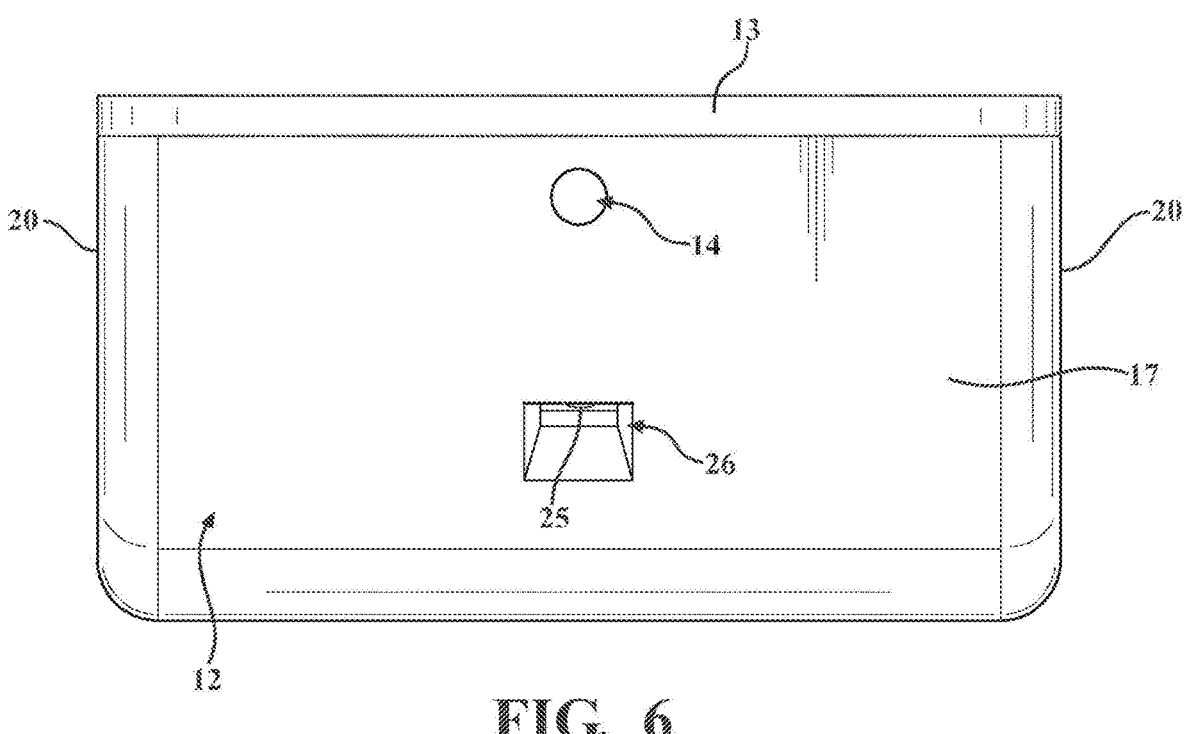
FIG. 6 is an end view of the sterilization apparatus of the FIG. 2.
Figure 7:
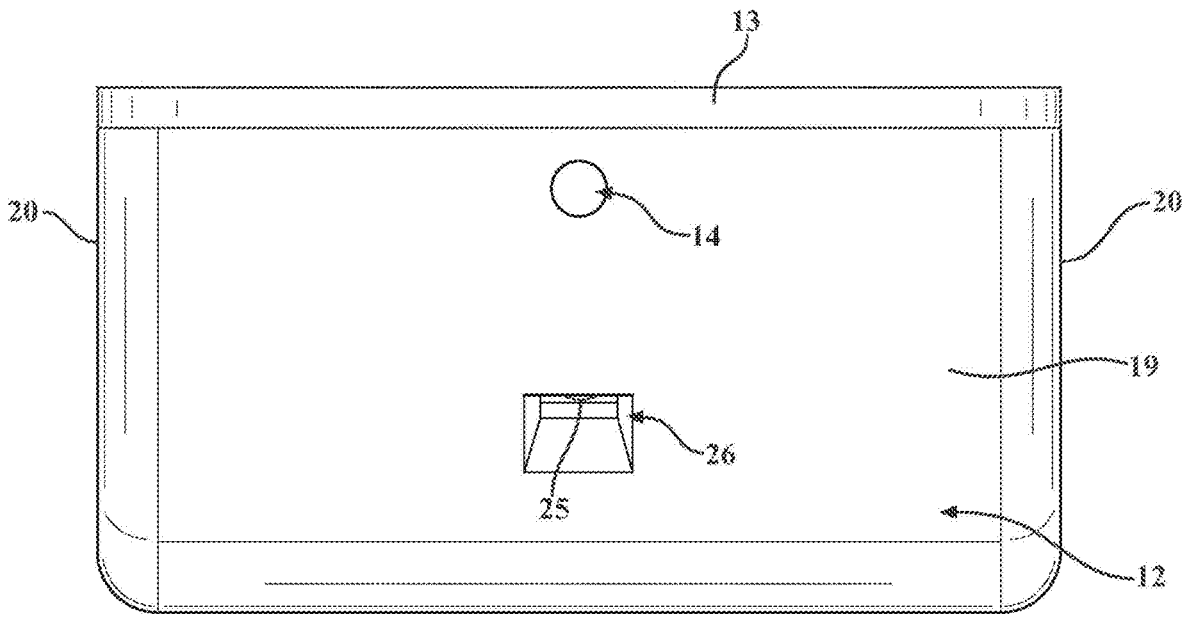
FIG. 7 is a lateral view of the sterilization apparatus of the FIG. 2, showing the side of the apparatus opposite that shown in FIG. 6.
Figure 8:
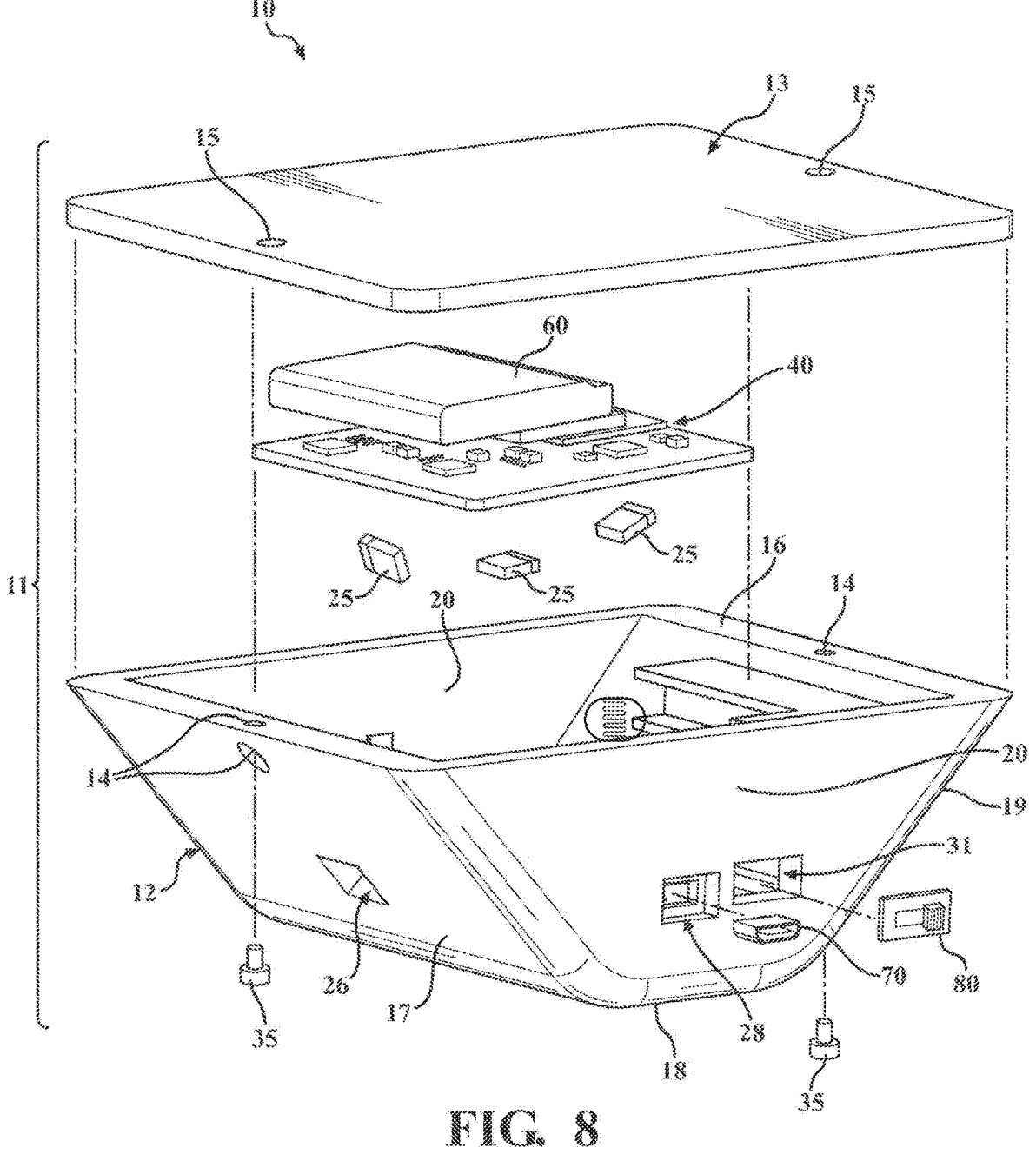
FIG. 8 is an exploded perspective view of the sterilization apparatus of the present invention.
Figures 9, 10:
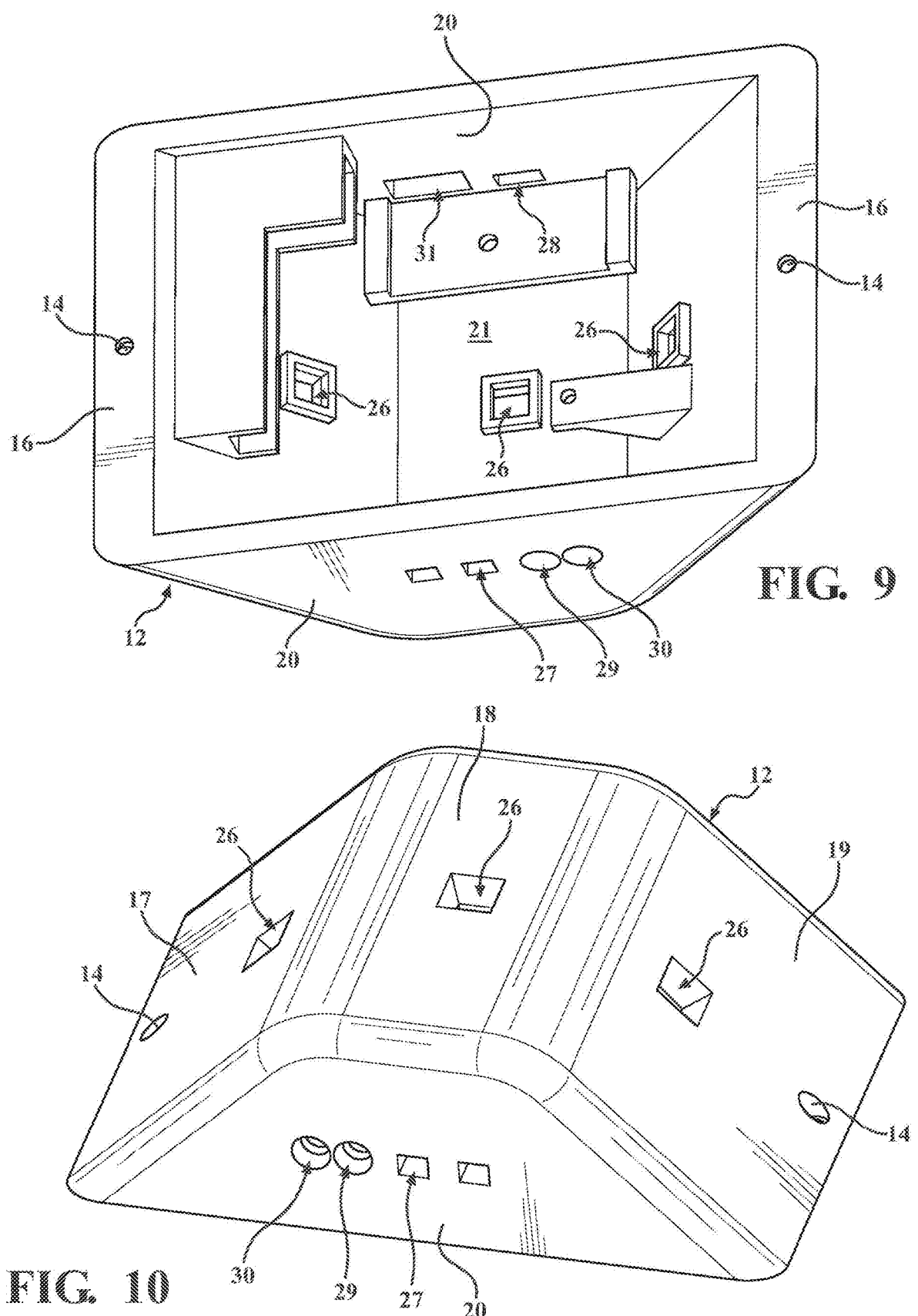
FIG. 9 is a top-down perspective view of the body portion of the housing.
FIG. 10 is a bottom-down perspective view of the body portion of the housing.
Figure 11:
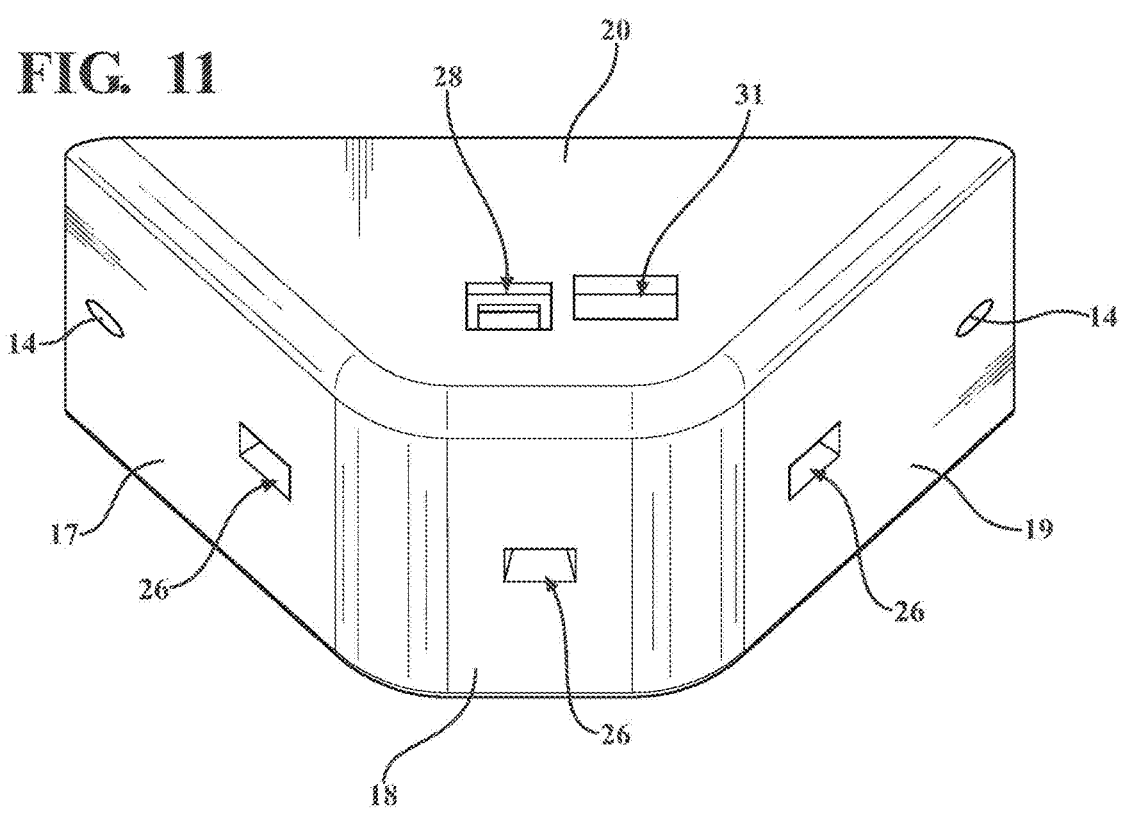
FIG. 11 is a bottom-up perspective view of the body portion of the housing.

Referring now to the drawings, where like numerals refer to like or corresponding parts throughout the several views, there is disclosed a UV-C sterilization apparatus for a confined space.

The confined space of the exemplary embodiment is one with cubic dimensions of approximately 2 feet or less, and has a closure which can be selectively positioned between a closed position, wherein the confined space is fully enclosed, and an opened position, wherein the confined space is accessible from an exterior thereof. By way of example and not of limitation, the confined space may be one of a glovebox or a center console in a passenger automobile. The closure may be one which is manually-operable and/or automatically moved between the closed and opened positions. Of course, it will be appreciated that the apparatus and method as described herein may be modified to function in other confined spaces, including confined spaces with cubic dimensions different from the exemplary embodiment.

With reference to FIG. 1 in particular, there is shown an exemplary automobile glovebox of conventional design and construction, according to which the confined space 1 is defined by a bottom surface 3 and walls 4, 5, and 6. Per convention, the wall 6 facing the interior cabin of the automobile also constitutes the closure, the entire glovebox assembly being pivotal so that the wall/closure 6 can be selectively moved in the directions of arrows A between an opened position (shown in FIG. 1) and a closed position (not shown) in which the glovebox pivots into the dashboard 7 and the wall/closure 6 sits securely against the dashboard, thereby preventing access to the space 1.

Of course, it will be appreciated by those skilled in the art that a glovebox of the foregoing construction is only exemplary of one kind of confined space to which the present invention is suited. As mentioned, an automobile's center console is another such confined space. In respect of that type of confined space, the closure is more typically a separate lid or cover which pivots between opened and closed positions to expose or seal the confined space, respectively. Still other confined spaces to which the present invention may be suited are stand-alone containers, desk drawers, cupboards, or any other confined space which can be selectively closed and opened and the interior dimensions of which are such that the invention as described herein is capable of sterilizing via UV-C radiation in the manner herein disclosed.

Referring next to FIGS. 2-11, the UV-C sterilization apparatus 10 of the present invention comprises a housing 11 dimensioned to fit within a confined space, such as, for instance, the glovebox as previously described. According to the illustrated embodiment, the housing 11 is formed of two mating portions: a body portion 12 and a cover portion 13 which is secured to the body portion, such as by means of bolts or screws 35 received through openings 14 in the body portion 12 and secured in threaded openings 15 in the cover portion 13. Of course, it is also envisioned that the body 12 and cover 13 portions could be secured together in any conventional manner. Where the apparatus 10 utilizes battery power, for instance, it may be desirable to connection with portions 12, 13 with tabs, hinges, etc. in order to make the battery/batteries more easily accessible to the user.

Body portion 12 is rectangular in top plan-view and is characterized by a trapezoidal cross-section in longitudinal side view. Top surface 16 of the body portion 12 opposes the cover portion 13 and defines a flat or planar surface, while the opposite, bottom of the body portion 12 is characterized by three adjacent surfaces 17, 18, 19 which are each oriented at a different angle relative to the others. The intermediate of these surfaces 18 is disposed generally parallel to the top surface 16, while surfaces 17 and 19 are each inclined upwardly toward the top surface 16 and away from the intermediate surface 18.

Angled surfaces 17, 18, 19 and sidewalls 20 together define an interior area 21 of the body portion 12. Interior area 21 houses the various components described hereafter. Upon securement of the cover portion 13 to the body portion 12, this interior area 21 is effectively sealed against the external environment.

Cover portion 13, as shown, is an essentially planar, rectangular element the dimensions of which correspond to the dimensions of the body portion 12 at the top surface 16 thereof.

Housing 11, including the body 12 and cover 13 portions, may be made from any suitable material though, in the illustrated embodiment, housing is fashioned from a polymer, and more particularly from a thermoplastic polymer such as ABS.

Still referring to FIGS. 2-11, the housing 11 supports at least one sensor operative to detect when the closure is in each of the closed and opened positions, at least one source operative to emit UV-C light for irradiating the confined space, and a controller.

Per the illustrated embodiment, at least three UV-C light sources are provided, in the form of micro-LEDs 25 each arranged to emit UV-C light in different directions relative to each other. More specifically, the at least three UV-C light sources 25 are each positioned within the interior area 21 adjacent one of the openings 26 provided through each of the surfaces 17, 18, and 19 of the body portion 12.

Controller, per the illustrated embodiment, takes the form of a printed circuit board (PCB) 40.

The above-referenced at least one sensor may be a photosensor sensor, an infrared sensor, an ultrasonic sensor, or any combination thereof. Other sensors may also be substituted for the foregoing, or any of them, subject only to the requirement that such sensor(s) be operative to detect when the closure is in the closed and open positions thereof, as hereafter described.

Each such sensor is connected to the PCB 40 and disposed relative to the housing so as to be capable of detecting light or objects outside the housing, whether in the manner herein described in connection with the exemplary embodiment or in a manner corresponding to the conventional operation of such other sensor(s) that may be employed.

Per the exemplary embodiment, the at least one sensor is a photosensor operative to detect when the closure is in each of the closed and opened positions by detecting the level of ambient light in the confined space. More particularly, the photosensor is, in the illustrated embodiment, a photoresistor 50 operatively coupled to the PCB 40. As shown, the photosensor is disposed on the outside of the housing 12; an opening 27 therethrough permits the photosensor to be electrically connected to the PCB.

The PCB 40 is programmed to recognize one or more predefined resistance thresholds—corresponding to the amount of ambient light in the confined space when the closure is opened, closed, or both—as reflecting that the closure is in one or more of the opened or closed conditions. More particularly, the PCB 40 is programmed to determine the closure to be in the closed position when the electrical resistance through the photoresistor 50 increases to at least a first predetermined value, and to determine the closure to be in the open position when the electrical resistance through the photoresistor 50 decreases to a value greater than a predefined percentage of deviation from the first predetermined value. According to the exemplary embodiment, this predefined percentage is approximately 5%. Of course, other percentages of deviation may be selected if more or less resistance is deemed indicative of closure opening.

While the first predetermined value may be established during manufacture of the apparatus and programmed in the PCB at that time as a fixed and unchangeable value, it is contemplated that, per the illustrated embodiment, the PCB is programmed with a calibration mode for the user to establish or adjust the first predetermined electrical resistance value. According to this embodiment, a user-actuatable push-button 55, operatively coupled to the PCB, is provided for entering the calibration mode. In the illustrated embodiment, the PCB is programmed to initiate the calibration mode when the push-button 55 is depressed for at least 3 seconds. Initiation of calibration mode is indicated by a green LED 56 disposed near the photoresistor 50, which LED 56 the PCB causes to flash rather than illuminate steadily. During calibration mode, the user is given a period of time to move the closure to its closed position. In the illustrated embodiment, this period of time is approximately 10 seconds. Thereafter, the PCB deems the closure to be closed and commences measuring the electrical resistance through the photoresistor during a finite period of time. In the exemplary embodiment, this finite period of time is approximately 10 seconds. At the end of this period of time, the PCB assigns the measured electrical resistance as the first predetermined value. In other words, the PCB is operative to establish this measured electrical resistance value as the first predetermined electrical resistance value—i.e., as the electrical resistance value corresponding to the closure being in the closed position thereof—and to record this value in the PCB's memory as the reference value for deeming the closure to be in the closed position.

Optionally, the PCB may be programmed during manufacture with an electrical resistance "ceiling" value which is predetermined to represent a generic "closed" position of the closure. According to this embodiment, calibration mode is still employed to set the first predetermined value more precisely to the particular confined space with which the apparatus is being used. However, the "ceiling" value is referenced by the PCB during calibration and compared to a measured electrical resistance value to determine whether the user has in fact placed the closure in the closed position thereof during the period of time (e.g., 10 seconds) allotted for that to occur. Further to this embodiment, at the start of the finite period of time (e.g., 10 seconds) of the calibration mode the PCB compares the electrical resistance value measured at the start of the finite period. If that measured electrical resistance value is equal to or less than the "ceiling" value, then calibration is terminated without establishing the first predetermined electrical resistance value. The PCB is programmed, in this case, to cause the red LED to flash or blink a predefined number of times (e.g., 4) to indicate that calibration was aborted. The user may enter the calibration mode subsequently to make one or more further attempts to set the first predetermined electrical resistance value.

The predefined "ceiling" value is, per the exemplary embodiment, the median or mean electrical resistance value for a variety of confined spaces representative of the type with which the apparatus of the invention is intended to be employed. As will be appreciated by those skilled in the art, establishment of this "ceiling" value may, for instance, be accomplished by measuring the electrical resistance values of a photoresistor in each a variety of confined spaces when their closures are in the closed position, and then determining the median or mean of those values.

Once the first predetermined electrical resistance value is established via the calibration mode, then the calibration mode is terminated. In conjunction with this, the green LED 56 returns to being steadily illuminated, reflecting that the device is on but no longer in calibration mode.

As noted above, the first predetermined value may also be may be established during manufacture, whether or not the calibration mode described above is part of the apparatus's features. In either case, the first predetermined value so established will be understood to be established in the same manner as, and will therefore be identical to, the "ceiling" value. It will be appreciated that, where the first predetermined value is established during manufacture and the apparatus does not feature a calibration mode, there is no need for a predefined "ceiling" value. On the other hand, where the apparatus features the above-described calibration mode, it will be understood that the "ceiling" value and first predetermined value, if established during manufacture as a user-adjustable value, will be the same.

It will be understood from the descriptions provided herein that at least three possible embodiments of the apparatus of the present invention are contemplated in respect of establishing a value indicative of the closure being in the closed position. First, an embodiment where the first predetermined value is established during manufacture and constitutes a fixed and unchangeable value. Second, an embodiment where the first predetermined value is established during manufacture and constitutes a value which may be adjusted by the user via the calibration mode. Per this embodiment, the first predetermined value also constitutes the "ceiling" value. If the calibration mode is not employed by the user, then the apparatus will operate using the first predetermined value as established during manufacture. Finally, an embodiment where the first predetermined value is undefined until the user employs the calibration mode. Per this embodiment, it will be understood that the apparatus will only operate to sterilize the confined space once the first predetermined value is set. Also per this embodiment, the apparatus may be programmed with the "ceiling" value as described above. Alternatively, the apparatus may simply be programmed to provide a finite period of time for the user to move the closure to the closed position, as described above.

The apparatus includes means for connecting to a power source to provide operating power. In one embodiment, these means comprise at least wiring for connecting to the PCB 40 one or more batteries 60 which is disposed in the housing 11. These one or more batteries may be "single-use" or rechargeable in nature. If rechargeable, then it will be appreciated that means must also be provided to permit recharging of the battery or batteries. Such means may include any conventional means suited to the purpose, and will include means, accessible to a user from the exterior of the housing, to connect the apparatus to an external power source to provide power for recharging the battery or batteries. In the illustrated embodiment, the one or more batteries 60 consist of a Li-ion rechargeable battery. A micro-USB port 70 is provided, accessible via an opening 28 in the body portion 12 of housing 11, via which the one or more batteries 60 may be recharged using a compatible power cable and an external power source, such as a wall outlet (e.g., 120V or 220V), a 12V automobile outlet, outlet or the battery of an automobile.

The micro-USB port 70 will be understood to be of conventional construction and to be operatively connected to the one or more batteries via the PCB 40.

Where a rechargeable battery or batteries are used, it will be understood that the PCB 40 will be capable of monitoring the charge state of such battery or batteries, and that the apparatus 10 may include a light 57 or other indicator visible from the exterior of the housing 11 to at least indicate to a user when the battery or batteries are determined to have a charge state that is low enough to warrant recharging. Per the exemplary embodiment, the light 57 takes the form of a red LED disposed next to the photoresistor 50 and green LED 56. The red LED 57 is coupled to the PCB, which is operative to cause the LED 57 to be illuminated when the battery or batteries are determined, via conventional electronics, to have a charge state that is low enough to warrant recharging. Openings 29 and 30 in the housing 12 permit the LEDs 56 and 57 to be operatively connected to the PCB.

An externally actuatable power switch 80 is also provided, the switch 80 being operably connected to the PCB via an opening 31 in the housing 12 so as enable a user to manually turn the apparatus on and off, thereby allowing manual control over whether and when the device is functional. In the illustrated embodiment, the switch 80 is disposed adjacent the micro-USB port 70. As stated previously, PCB 40 is operative to illuminate the green LED 56 in a steady state when the apparatus 10 is in an "on" state.

Figure 12:
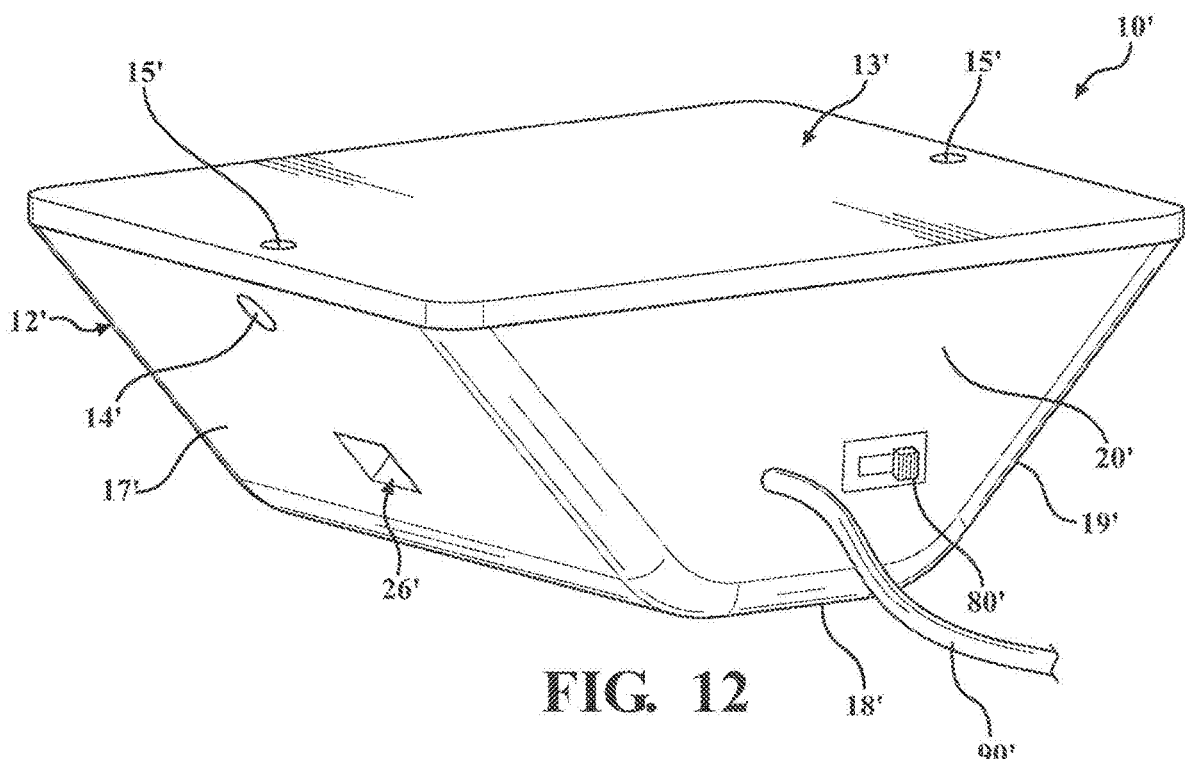
FIG. 12 is a quartering perspective view of the sterilization apparatus of the present invention, according to another embodiment thereof.

Per an alternative embodiment, shown in FIG. 12, the apparatus 10' may be exclusively externally powered, in which case the means for connecting to a power source may comprise wiring 90 for connecting the apparatus 10' to an external power source. According to the illustrated example, wherein the apparatus is adapted to be disposed in the glovebox of an automobile, the external power source would be the automobile's battery (not depicted) and such wiring 90 would take the specific form of a wiring harness adapted for electrical connection with a wiring harness of the automobile. Preferably, though not necessarily, the apparatus 10' would still incorporate the power switch 80' and "on" indicator LED (not shown in FIG. 12) described above.

In all cases, the PCB 40 of the illustrated embodiment includes a driver which runs all components of the apparatus at 5V. Consequently, it will be appreciated that an appropriate transformer or converter will be needed to step the voltage to 5V.

Controller (e.g., PCB 40) is operative, as described above, to determine from the at least one sensor as to when the closure is in each of the closed and opened positions, to activate the at least one UV-C light source (e.g., micro-LEDs 25) to irradiate the confined space for a first fixed period of time when the closure moves from the opened position to the closed position, and to prevent the at least one UV-C light source from irradiating the confined space when the closure moves from the closed position to the opened position. Further, controller (e.g., PCB 40) is operative to periodically activate the at least one UV-C light source to irradiate the confined space for at least a second fixed period of time, the periodic activation occurring following the first fixed period of time and continuing for so long as the closure remains in the closed position.

In the exemplary embodiment, the first fixed period of time is approximately three minutes, that period of time having been determined to be sufficient for an apparatus according to the illustrated example to provide an effective dose of UV-C irradiation to the contents of a confined space of approximately 2 cubic feet or less.

Also according to the exemplary embodiment, the second fixed period of time is approximately 3 minutes, while the period activation of the UV-C light source (e.g., the micro-LEDs 25) is approximately every 60 minutes.

According to the illustrated embodiment more specifically, wherein a sensor in the form of a photosensor—and, even more particularly, a photoresistor 50—is provided, controller (e.g., PCB 40) is operative to determine from changes in electrical resistance through the photoresistor when the closure is in the closed position. Still more specifically, the controller (e.g., PCB 40) is programmed to determine that the closure is in the closed position when the electrical resistance to the photoresistor 50 increases to at least a first predetermined value (as established during manufacture or via the calibration mode described previously). On the other hand, the controller (e.g., PCB 40) is programmed to treat as indicating that the closure is being opened any decrease in resistance the value of which is greater than a predefined percentage of deviation from the first predetermined value. Upon such determination that the closure is being opened, the controller is programmed to immediately discontinue illumination from the UV-C light source(s).

Figure 13:
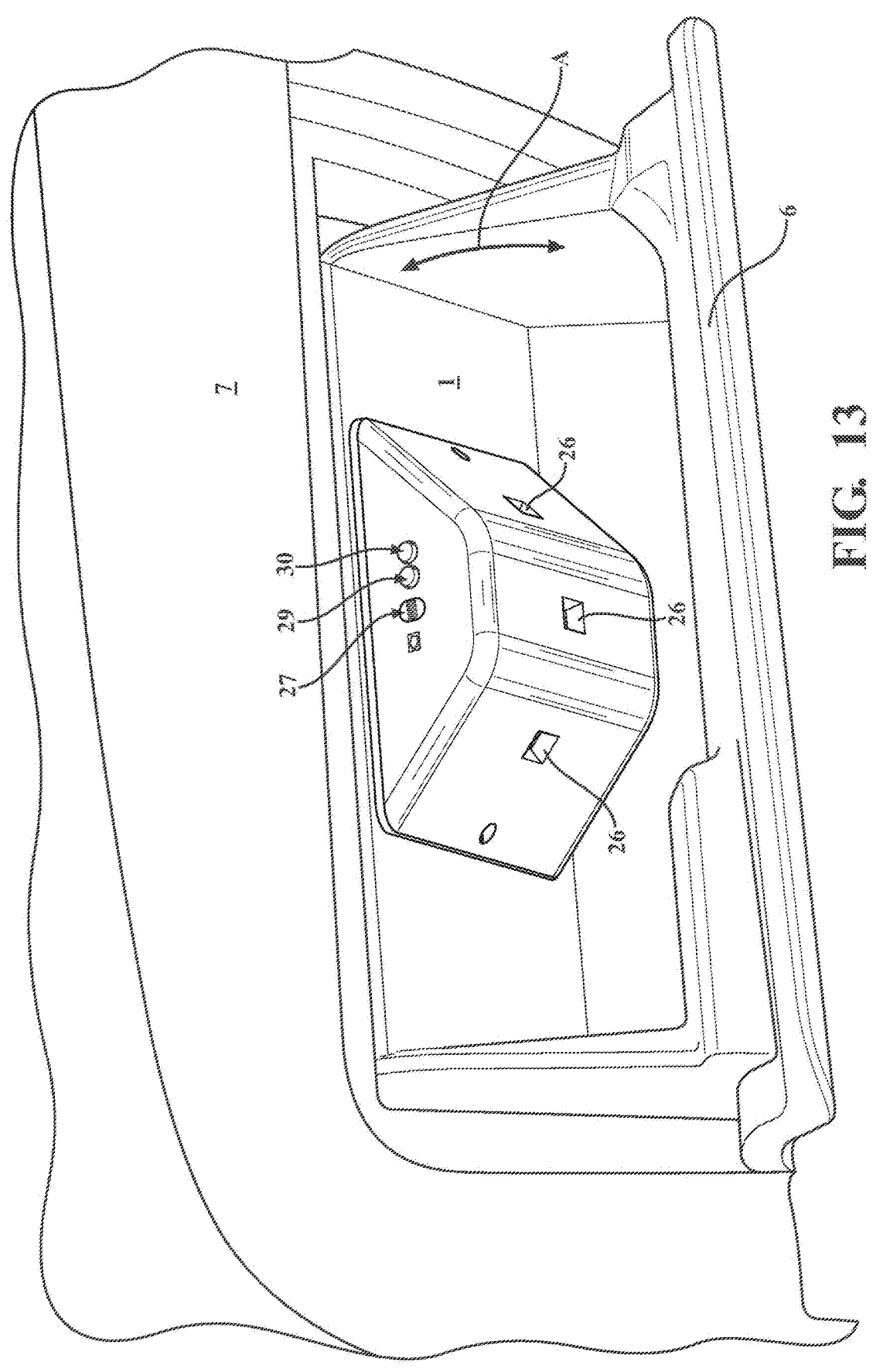
FIG. 13 is a perspective view of the sterilization apparatus of the present invention shown mounted in the glovebox of an automobile.

Referring next to FIG. 13, the sterilization apparatus 10 is shown in the exemplary environment of being disposed in a glovebox of an automobile. While any suitable means may be employed to secure the apparatus 10 in position, it is contemplated in the exemplary embodiment that hook-and-loop type fasteners may be employed between a surface of the glovebox and the cover 13 of the apparatus 10.

Figure 14:
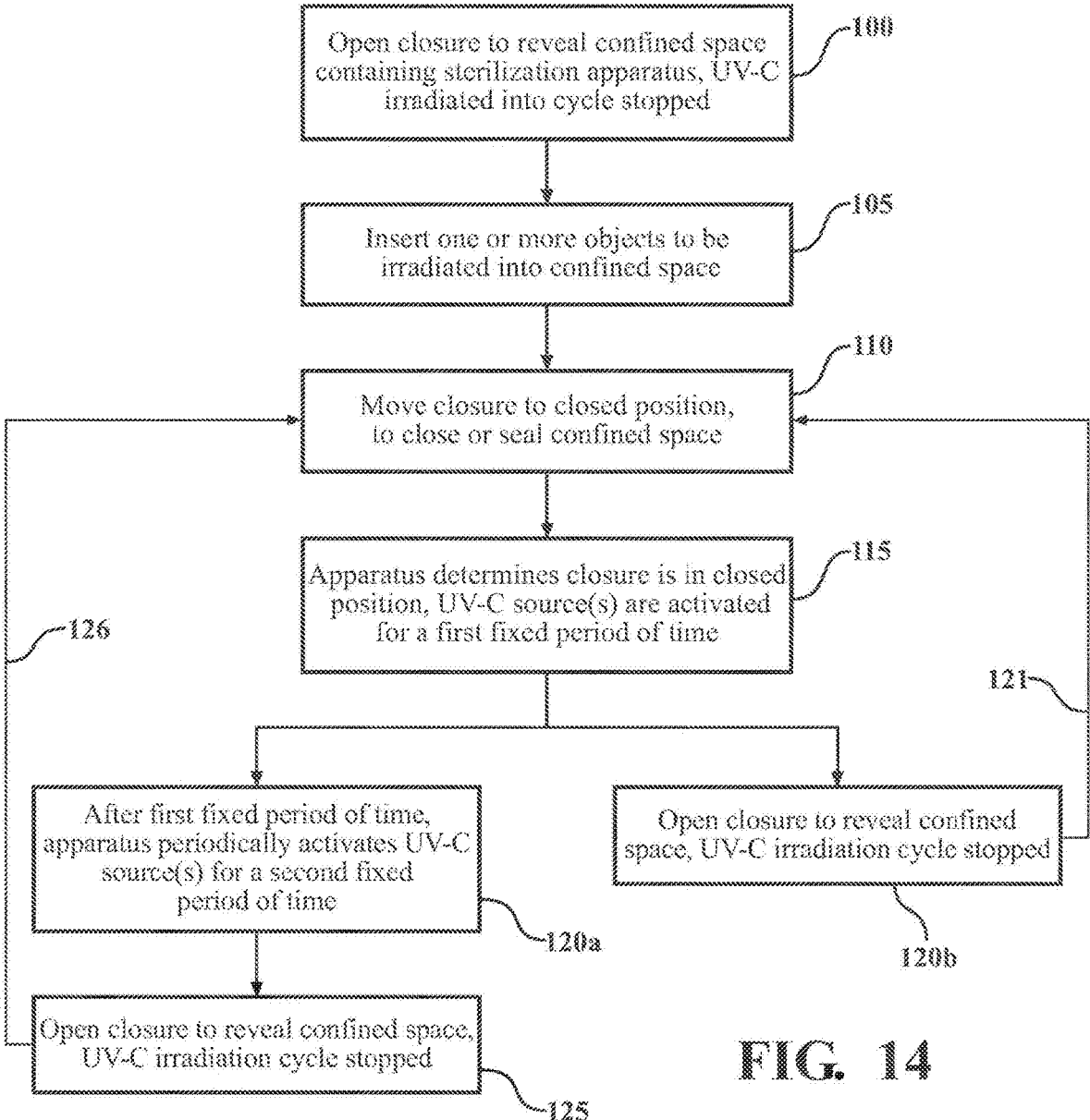
FIG. 14 is a diagram depicting the various steps in the method of operation of the present invention, according to an exemplary embodiment thereof.

Referring also to FIG. 14, the method of use of the apparatus described above is set out in further detail, using as an exemplary use the installation of that apparatus in an automobile's glovebox.

In a first step 100, the glovebox is opened to reveal the confined space containing the sterilization apparatus of the present disclosure, which has heretofore been positioned inside the glovebox and is connected to a power source (battery and/or external power). The sensor(s), whether the photosensor as heretofore described or another suitable sensor or sensors, detect a change in condition (e.g., ambient light) reflecting opening of the closure, and the input(s) generated by the sensor(s) (e.g., the change in electrical resistance heretofore described) is interpreted by the controller (e.g., the PCB) to represent the opening of the closure according to predefined threshold value associated with the sensor inputs. In the event the closure is interpreted as being open, the controller stops the irradiation cycle: that is, the controller discontinues all further operation of the one or more UV-C sources (e.g., micro-LEDs).

At this juncture, the user (e.g., automobile occupant) may place one or more items to be irradiated in into the confined space, as shown at step 105.

Upon the user's subsequently moving the closure to the closed position, as shown at step 110, the confined space is once again closed.

Next, in step 115, the apparatus determines that the closure is in the closed position. As discussed previously, this is accomplished by the sensor(s) in combination with the controller (e.g., PCB). Such sensor(s), whether the photosensor as heretofore described or another suitable sensor or sensors, detect a change in condition (e.g., ambient light) reflecting closing of the closure, and the input(s) generated by the sensor(s) (e.g., the change in electrical resistance heretofore described) is interpreted by the controller (e.g., the PCB) to represent the closing of the closure according to predefined threshold value associated with the sensor inputs. In the event the closure is interpreted as being closed, the controller starts the irradiation cycle; that is, the controller commences operation of the one or more UV-C sources (e.g., micro-LEDs) to emit UV-C irradiation for a first fixed period of time. As discussed previously, this first period of time is 3 minutes, following which the controller stops the UV-C source(s) from emitting radiation.

Subsequently, and for so long as the closure remains in the closed position, the controller commences operation of the one or more UV-C sources at regular intervals and for a fixed period each time. This is shown in Step 120a. As discussed above, these periodic activations may, per the exemplary embodiment, occur every 60 minutes and last for a fixed period of time of 3 minutes. Of course, it will be appreciated that the periodicity of these activations may be increased or decreased and, moreover, that the fixed period of time may be changed.

As shown at Step 120b, if the closure is determined by the controller (operating in conjunction with the sensor(s), as described above) to be opened before the step 120a, then the controller (e.g., PCB) operates to discontinue all further operation of the one or more UV-C sources (e.g., micro-LEDs). At this point, the process of the present invention is initiated again only when the closure is again determined to have been moved to the closed position thereof. This is depicted in FIG. 14 by the arrow 121 from step 120b proceeding to step 110, from which the process then proceeds stepwise to step 115, etc.

As shown at step 125, the process of step 120a, once initiated, will continue until the closure is determined by the controller (operating in conjunction with the sensor(s), as described above) to be opened. At that point, the controller (e.g., PCB) operates to discontinue all further operation of the one or more UV-C sources (e.g., micro-LEDs). Thereafter, the process of the present invention is initiated again only when the closure is again determined to have been moved to the closed position thereof. This is depicted in FIG. 14 by the arrow 126 from step 125 proceeding to step 110, from which the process then proceeds stepwise to step 115, etc.

It is to be understood that the disclosed embodiments represent presently preferred examples of how to make and use the invention, but are intended to enable rather than limit the invention. Variations and modifications of the illustrated examples in the foregoing written specification and drawings may be possible without departing from the scope of the invention.

It should further be understood that to the extent the term "invention" is used in the written specification, it is not to be construed as a limiting term as to number of claimed or disclosed inventions or discoveries or the scope of any such invention or discovery, but as a term which has long been used to describe new and useful improvements in science and the useful arts. The scope of the invention supported by the above disclosure should accordingly be construed within the scope of what it teaches and suggests to those skilled in the art, and within the scope of any claims that the above disclosure supports.

The claims are representative of the invention and are not intended to limit the claimed invention with respect to other features which are supported by or might become apparent from the description, and which might be claimed subsequently.

The invention in which an exclusive property or privilege is claimed is defined as follows:

1. A UV-C sterilization apparatus for a confined space having a closure which can be selectively positioned between a closed position, wherein the confined space is fully enclosed, and an opened position, wherein the confined space is accessible from an exterior thereof, the UV-C sterilization apparatus comprising:

means for connecting the apparatus to a power source to provide operating power to the apparatus; and a housing dimensioned to fit within the confined space, the housing supporting:

at least one sensor operative to detect when the closure is in the closed position and/or when the closure is not in the closed position;

at least one source operative to emit UV-C light for irradiating the confined space; and a controller connected to the at least one sensor and the at least one UV-C light source, the controller operative to:

determine from the at least one sensor when the closure is in the closed position and when the closure is not in the closed position;

activate the at least one UV-C light source to irradiate the confined space for a first fixed period of time when it is determined that the closure has gone from the opened position to the closed position;

periodically activate the at least one UV-C light source to irradiate the confined space for at least a second fixed period of time, the periodic activation occurring following the first fixed period of time for so long as the closure remains in the closed position; and prevent the at least one UV-C light source from irradiating the confined space when it is determined that the closure is no longer in the closed position.

2. The apparatus of claim 1, wherein the means for connecting the apparatus to a power source are operative to connect the apparatus to one or more batteries disposed in the housing.

3. The apparatus of claim 1, wherein the means for connecting the apparatus to a power source are operative to connect the apparatus to one or more rechargeable batteries disposed in the housing.

4. The apparatus of claim 1, wherein the means for connecting the apparatus to a power source are operative to connect the apparatus to a power source external to the apparatus.

5. The apparatus of claim 1, wherein the housing supports at least three UV-C light sources arranged to emit UV-C light in different directions relative to each other.

6. The apparatus of claim 5, wherein the housing is characterized in that the at least three UV-C light sources are each positioned in a surface of the housing which is oriented at a different angle relative to the others of the UV-C light sources.

7. The apparatus of claim 1, wherein the at least one sensor is a photosensor.

8. The apparatus of claim 7, wherein the photosensor is a photoresistor.

9. The apparatus of claim 8, wherein the controller is programmed to determine the closure to be in the closed position when electrical resistance through the photoresistor increases to at least a first predetermined value, and to determine the closure to not be in the closed position when the electrical resistance through the photoresistor decreases to a value greater than a predefined percentage of deviation from the first predetermined value.

10. The apparatus of claim 9, wherein the predefined percentage of deviation is approximately 5%.

11. The apparatus of claim 9, wherein the apparatus has a calibration mode for establishing the first predetermined value, according to which calibration mode the controller is operative to measure the electrical resistance through the photoresistor during a finite period of time when the closure is in the closed position, and to establish the first predetermined value as an electrical resistance measurement taken during said finite period of time.

12. The apparatus of claim 11, wherein said finite period of time is approximately 10 seconds.

13. The apparatus of claim 11, wherein said finite period of time is preceded by a predefined period of time allowing for the closure to be moved to the closed position.

14. The apparatus of claim 11, wherein the controller is programmed with an electrical resistance "ceiling" value, and wherein the controller is further programmed to (a)

compare the electrical resistance "ceiling" value with the measured electrical resistance at the start of the finite period of time, and (b) terminate the calibration mode without establishing the first predetermined electrical resistance value if the measured electrical resistance at the start of the finite period of time is equal to or less than the "ceiling" value.

15. The apparatus of claim 1, wherein the housing is dimensioned to fit within a confined space having cubic dimensions of approximately 2 feet or less, and wherein further the first fixed period of time is approximately three minutes.

16. The apparatus of claim 15, wherein the second fixed period of time is approximately three minutes and the periodic activation of the at least one UV-C light source is approximately every 60 minutes.

* * * * *